(12) United States Patent
Richards

(10) Patent No.: US 11,154,674 B2
(45) Date of Patent: Oct. 26, 2021

(54) RESPIRATORY THERAPY APPARATUS

(71) Applicant: SMITHS MEDICAL INTERNATIONAL LIMITED, Kent (GB)

(72) Inventor: Fredrick M Richards, Plymouth, MA (US)

(73) Assignee: SMITHS MEDICAL INTERNATIONAL LIMITED, Ashford (GB)

( * ) Notice: Subject to any disclaimer, the term of this patent is extended or adjusted under 35 U.S.C. 154(b) by 726 days.

(21) Appl. No.: 15/522,873

(22) PCT Filed: Sep. 30, 2015

(86) PCT No.: PCT/GB2015/000278
§ 371 (c)(1),
(2) Date: Apr. 28, 2017

(87) PCT Pub. No.: WO2016/075426
PCT Pub. Date: May 19, 2016

(65) Prior Publication Data
US 2017/0319800 A1    Nov. 9, 2017

(30) Foreign Application Priority Data

Nov. 12, 2014    (GB) ..................... 1420127

(51) Int. Cl.
*A61M 16/00*    (2006.01)
*A61M 16/20*    (2006.01)
(Continued)

(52) U.S. Cl.
CPC .... *A61M 16/0006* (2014.02); *A61M 16/0003* (2014.02); *A61M 16/0866* (2014.02);
(Continued)

(58) Field of Classification Search
CPC .............. A61M 16/00; A61M 16/0003; A61M 16/0006; A61M 16/0057; A61M 16/0488;
(Continued)

(56) References Cited

U.S. PATENT DOCUMENTS 6,253,766 B1 * 7/2001 Niles ..................... A61M 16/08
128/204.24
8,025,054 B2    9/2011 Dunsmore et al.
(Continued)

FOREIGN PATENT DOCUMENTS

| EP | 1078646 A1 | 2/2001 |
| EP | 1772165 A1 | 4/2007 |
| EP | 1908489 A1 | 4/2008 |

OTHER PUBLICATIONS

PCT International Search Report and Written Opinion, dated Mar. 21, 2016, PCT/GB2015/000278.

*Primary Examiner* — Joseph D. Boecker
(74) *Attorney, Agent, or Firm* — Louis Woo

(57) ABSTRACT

A respiratory therapy apparatus includes a rocker mechanism (101, 110, 111, 112) that provides an oscillating resistance to expiration. The apparatus also includes an air entrainment arrangement (200) at its air inlet (3) having a ring orifice (214) connected via a gas inlet (4) to a source (119) of oxygen at elevated pressure. The oxygen emerging around the ring orifice (214) entrains ambient air and supplies this as a continuous flow of respiratory gas to the patient interface (2) to provide a positive airway pressure.

6 Claims, 6 Drawing Sheets

(51) Int. Cl.
*A61M 16/08* (2006.01)
*A63B 23/18* (2006.01)
*A61M 16/12* (2006.01)
*A61M 16/10* (2006.01)

(52) U.S. Cl.
CPC .......... *A61M 16/20* (2013.01); *A61M 16/208* (2013.01); *A63B 23/18* (2013.01); *A61M 16/101* (2014.02); *A61M 16/127* (2014.02); *A61M 2016/0036* (2013.01)

(58) Field of Classification Search
CPC .............. A61M 16/08; A61M 16/0858; A61M 16/0866; A61M 16/101; A61M 16/12; A61M 16/127; A61M 16/20; A61M 16/208; A61B 5/087; A61B 5/097; A63B 23/18

See application file for complete search history.

(56) References Cited

U.S. PATENT DOCUMENTS

| | | | | |
|---|---|---|---|---|
| 2003/0234017 | A1* | 12/2003 | Pelerossi | A63B 21/00196 128/201.26 |
| 2008/0078383 | A1* | 4/2008 | Richards | A61M 16/08 128/203.12 |
| 2008/0110451 | A1 | 5/2008 | Dunsmore | |
| 2019/0366023 | A1* | 12/2019 | Alizoti | A61M 16/0057 |

* cited by examiner

RESPIRATORY THERAPY APPARATUS

This invention relates to respiratory therapy apparatus of the kind including a respiratory therapy device of the kind having a patient interface and a mechanism arranged to produce an oscillating resistance to expiratory flow through the device Patients with respiratory system diseases (such as asthma, COPD, cystic fibrosis or the like) may suffer from hyper-secretion of mucus as a prominent pathophysiological feature. Moreover, those patients with hyper-secretion often also have impaired mucus transport. This imbalance between mucus transport and secretion results in mucus retention in the respiratory system.

Vibratory respiratory positive expiratory pressure (V-PEP) or oscillatory PEP (O-PEP) devices are modern devices for applying chest physiotherapy. These devices apply chest physiotherapy by providing an alternating resistance to flow and have been found to be particularly effective. One example of such apparatus is sold under the trade mark Acapella (a registered trade mark of Smiths Medical) by Smiths Medical and is described in U.S. Pat. No. 6,581,598, U.S. Pat. No. 6,776,159, U.S. Pat. No. 7,059,324 and U.S. Pat. No. 7,699,054. Other vibratory respiratory therapy apparatus is available, such as "Quake" manufactured by Thayer, "AeroPEP" manufactured by Monaghan, "TheraPEP" manufactured by Smiths Medical, "IPV Percussionator" manufactured by Percussionaire Corp, and the "Flutter" and "Lung Flute" devices, amongst others. EP2636420 describes an oscillatory PEP device with a nebulizer. These devices are used by patients who suffer from mucus hyper-secretions and retention to help them clear the secretions from their lungs. It has been reported that some patients may benefit from playing a harmonica: http://denver.cbslocal.com/2015/03/03/colorado-patients-coping-with-copd-hum-on-the-harmonica-for-help/

The Acapella O-PEP device combines the principles of low-frequency oscillation and positive expiratory pressure by employing a counterweighted lever and magnet to produce oscillatory positive pressures during expiration. This generated oscillating positive pressure works by mechanically reducing the viscoelasticity of the sputum by breaking down the bonds of mucus macromolecules which, in turn, enhances mucociliary clearance.

One problem with these vibratory PEP therapy devices is that there are many patients who are unable to exhale with sufficient force to produce a beneficial effect. Such patients require external assistance to help move secretions.

It is an object of the present invention to provide alternative respiratory therapy apparatus.

According to the present invention there is provided respiratory therapy apparatus of the above-specified kind, characterised in that the therapy apparatus additionally includes an arrangement for generating a continuous flow of inspiratory respiratory gas to the patient, that the arrangement includes a gas inlet arranged to receive a supply of respiratory gas at elevated pressure, and that the arrangement provides a positive airway pressure to the patient interface.

The mechanism arranged to produce an oscillating resistance to expiratory flow may include a valve element on a rocker arm that opens and closes an opening during exhalation through the apparatus. The arrangement for generating a continuous flow of inspiratory respiratory gas may include an air entrainment device arranged to receive gas from the inlet such as to entrain air and deliver a positive pressure to the patient interface. The air entrainment device may include a ring orifice arranged to receive the gas at elevated pressure and to amplify inspiratory gas flow to the patient interface by entraining air through the orifice. The gas at elevated pressure may have an oxygen concentration at higher than atmospheric concentrations. The apparatus may include an air flow tube opening at one end into the patient interface and opening at its opposite end into the arrangement for generating a continuous flow of inspiratory respiratory gas to the patient, and the air flow tube opening into the mechanism arranged to produce an oscillating resistance to expiratory flow through the device at a location between the patient interface and the arrangement for generating a continuous flow of inspiratory respiratory gas.

Respiratory therapy apparatus according to the present invention will now be described, by way of example, with reference to the accompanying drawings, in which.

Figure 1:
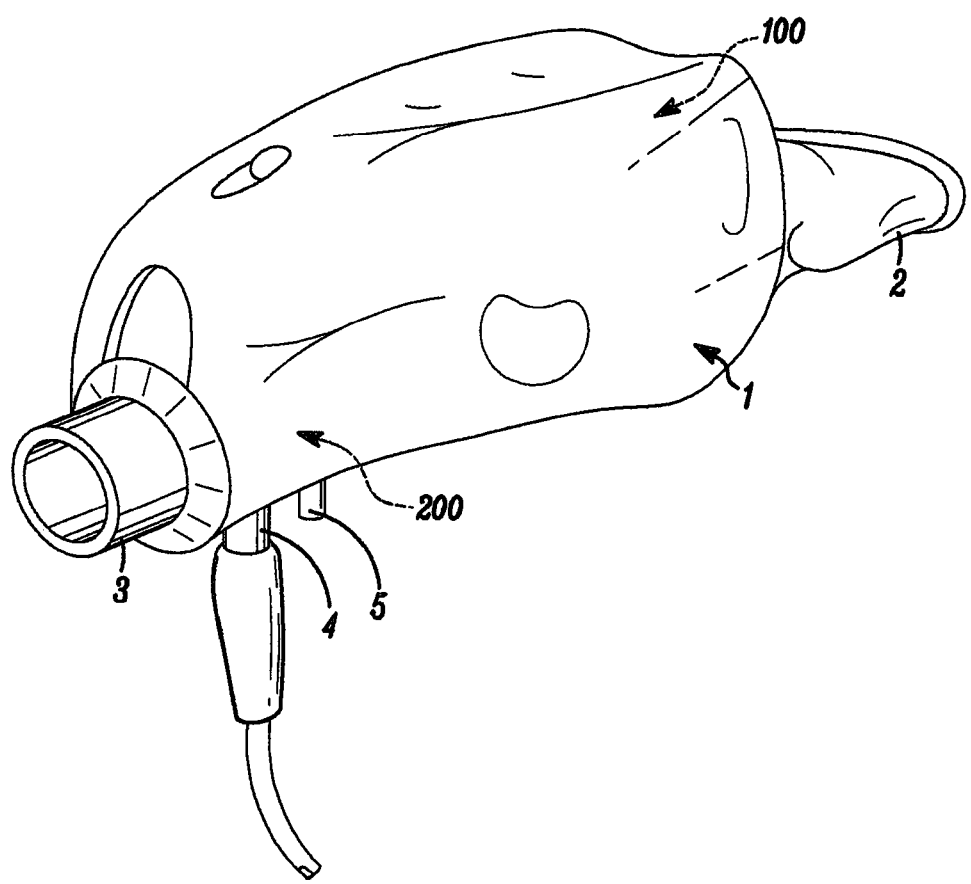
FIG. 1 is a perspective view showing the exterior of the apparatus from its machine end.

With reference first to FIG. 1, the apparatus has a housing 1 with a patient interface 2 at one end in the form of a mouthpiece, although it could include other interfaces such as, for example, a face mask or adaptor for connection to a tracheal tube. At its opposite end the housing 1 has an air inlet 3 open to atmosphere. The housing 1 encloses a series arrangement of an oscillatory O-PEP device 100 and an air entrainment device 200 that provides the air inlet 3. A side inlet port 4 and a pressure monitoring port 5 both open into the air entrainment device 200 as described in greater detail below.

Figure 2:
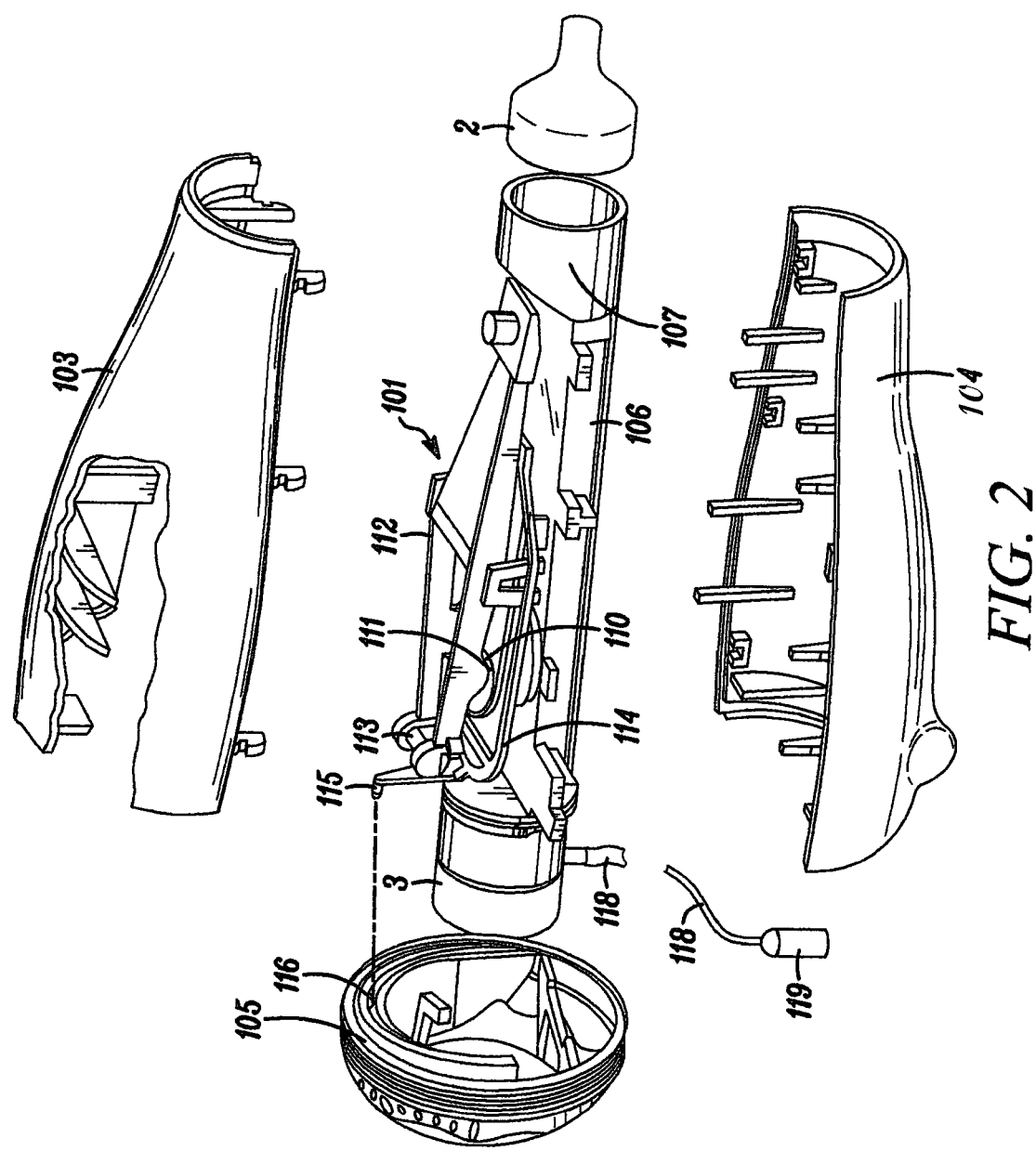
FIG. 2 is an exploded perspective view of the interior of the apparatus.

With reference now also to FIG. 2, the O-PEP device 100 is similar to an "Acapella" respiratory therapy device comprising a rocker assembly 101 contained within the outer housing 1 provided by an upper part 103 and a lower part 104 of substantially semi-cylindrical shape. The device 100 is completed by an adjustable dial 105 of circular section. The rocker assembly 101 includes an air flow tube 106 with a breathing inlet 107 at the end of the patient interface 2 and the inspiratory air inlet 3 at the opposite end including a one-way valve (not shown) that allows air to flow into the air flow tube 6 but prevents air flowing out through the inspiratory inlet. The air flow tube 106 has an outlet opening 110 with a non-linear profile that is opened and closed by a conical valve element 111 mounted on a rocker arm 112 pivoted midway along its length about a transverse axis. The air flow tube 106 and housing 1 provide a structure with which the rocker arm 112 is mounted. At its far end, remote from the breathing inlet 107, the rocker arm 112 carries an iron pin 113 that interacts with the magnetic field produced by a permanent magnet (not visible) mounted on an adjustable support frame 114. The magnet arrangement is such that, when the patient is not breathing through the device, the far end of the rocker arm 112 is held down such that its valve element 111 is also held down in sealing engagement with the outlet opening 110. A cam follower projection 115 at one end of the support frame 114 locates in a cam slot 116 in the dial 105 such that, by rotating the dial, the support frame 114, with its magnet, can be moved up or down to alter the strength of the magnetic field interacting with the iron pin 113. The dial 115 enables the frequency of operation and the resistance to flow of air through the device to be adjusted for maximum therapeutic benefit to the user. Other O-PEP devices may have different setting arrangements for adjusting operation of the device and may be graduated in other ways, such as in frequency.

When the patient inhales through the mouthpiece 2 air is drawn through the inspiratory inlet 3 and along the air flow tube 106 to the breathing inlet 107. When the patient exhales, the one-way valve in the inspiratory inlet 3 closes, preventing any air flowing out along this path. Instead, the expiratory pressure is applied to the underside of the valve element 111 on the rocker arm 112 causing it to be lifted up out of the opening 110 against the magnetic attraction, thereby allowing air to flow out to atmosphere. The opening 110 has a non-linear profile, which causes the effective discharge area to increase as the far end of the rocker arm 112 lifts, thereby allowing the arm to fall back down and close the opening. As long as the user keeps applying sufficient expiratory pressure, the rocker arm 112 will rise and fall repeatedly as the opening 110 is opened and closed, causing a vibratory, alternating or oscillating interruption to expiratory breath flow through the device. The construction and operation of the device is similar to that described in U.S. Pat. No. 6,581,598.

Figure 3:
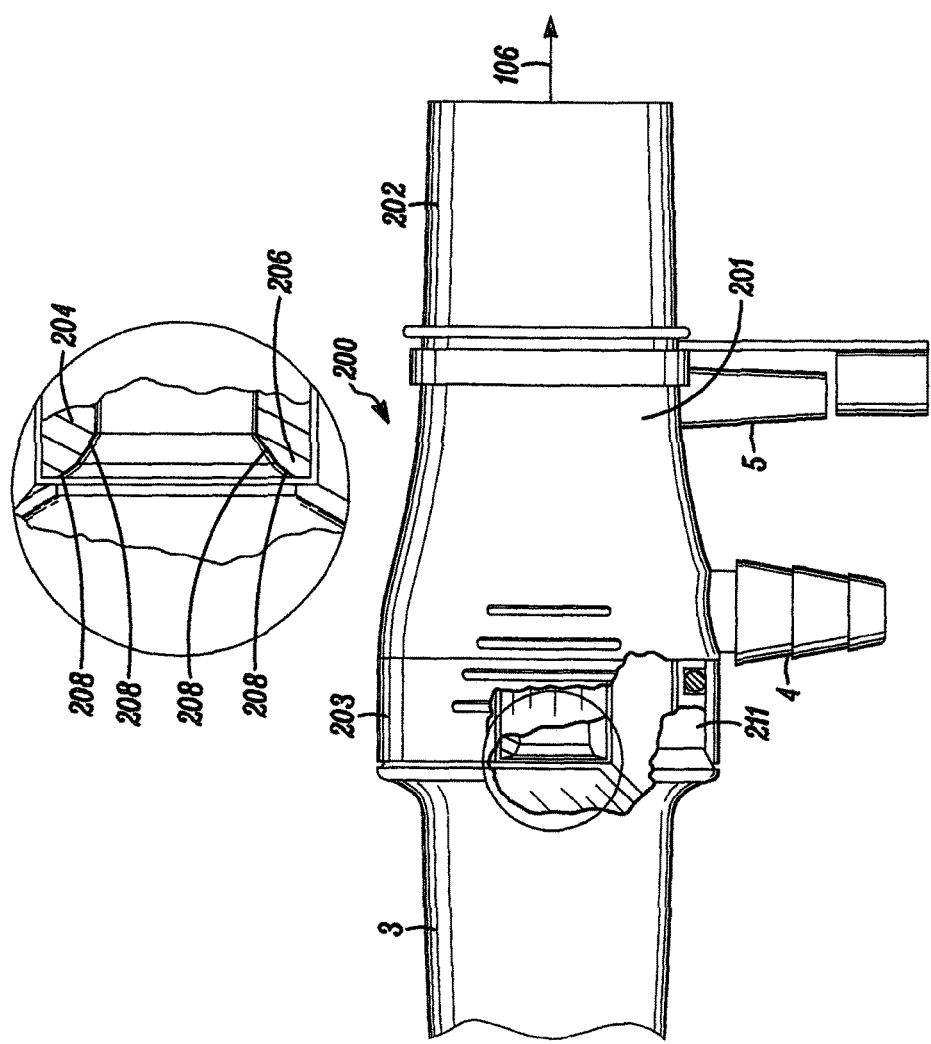
FIG. 3 is a partly cut-away side elevation view of the inspiratory air inlet and the air entrainment device of the apparatus.
Figure 4:
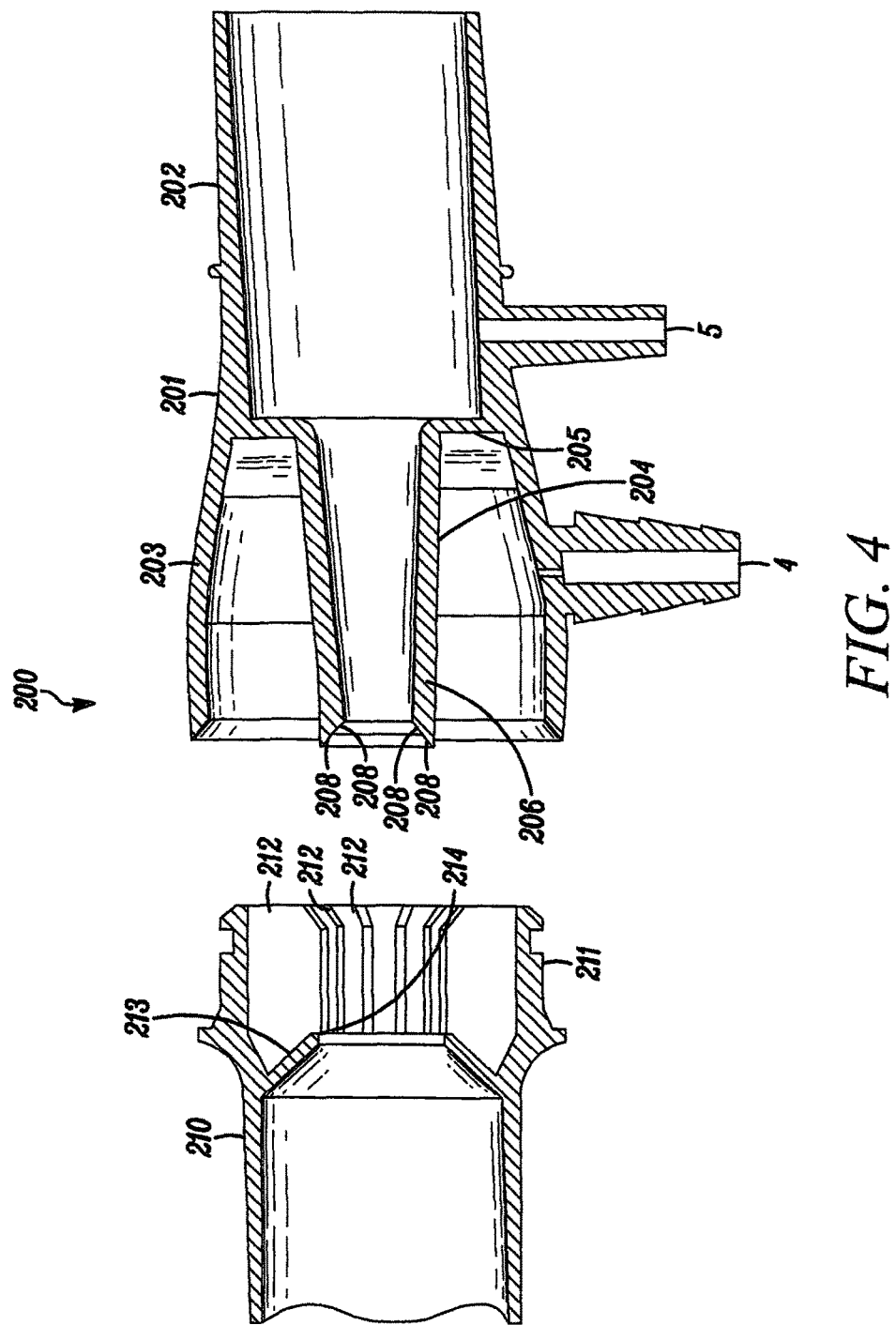
FIG. 4 is a sectional side elevation view of the air entrainment inlet showing the parts separated.
Figure 5:
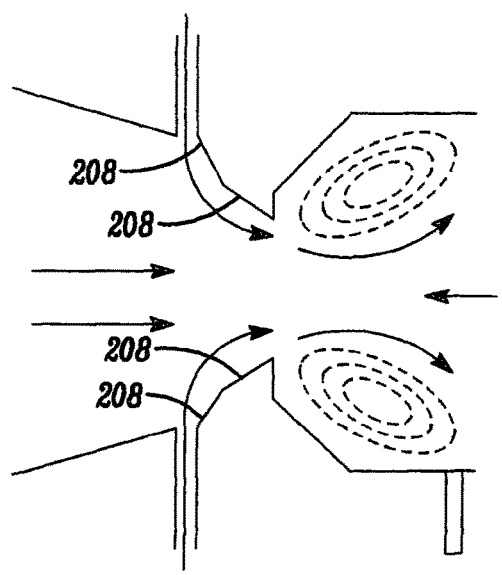
FIG. 5 shows schematically operation of the air entrainment inlet.

With reference now also to FIGS. 3 to 5, the inspiratory air inlet 3 is provided through the air entrainment arrangement or device 200, which, when in operation, acts to amplify the flow of atmospheric air into the air flow tube 106 and hence to the patient's respiratory system. This maintains a positive airway pressure (PAP) delivered to the patient. The one-way valve that prevents the patient exhaling through the air inlet 3 may be positioned rearwardly, to the left of the air entrainment device 200, that is between the air entrainment device and atmosphere, or it may be positioned on the opposite side of the air entrainment device, between this and the O-PEP device 100. Alternatively, the one-way valve may be omitted entirely if the air entrainment device 200 creates sufficient back pressure during use to restrict exhalation through the air inlet 3.

The entrainment device 200 includes a forward section 201 having a cylindrical portion 202 provided by towards its patient end and a frusto-conical portion 203 towards its rear end, the frusto-conical portion being arranged with its narrower end towards the patient. The inlet port 4 projects radially outwardly of the forward section 201 and has a barbed outer surface onto which an end of resilient gas tubing 118 (FIG. 2) can be pushed and retained. The inlet port 4 opens into the casing 201 towards its wider end. The pressure monitoring port 5 opens into the casing 201 on the patient side of the inlet port 4. An internal conduit 204 extends coaxially within the frusto-conical portion 203 of the casing 201 from a lateral support wall 205 located at the narrow end of the frusto-conical portion. The conduit 204 tapers slightly along its length from the wall 205, where it is wider, to its left-hand, free end 206, where it is narrower. The inside of the free end 206 is shaped with an inwardly-stepped Coanda profile 208. The entrainment device 200 also includes a rear section 210 having a forward end collar 211 fitted within the rear end of the frusto-conical portion 203. Several fins or vanes 212 are spaced around the inside of the rear section 210, the inner ends of the vanes contacting the outside of the conduit 204. An internal, frusto-conical wall 213 extends inwardly and rearwardly around the forward end of the vanes 212. The inner end of the wall 213 defines a ring orifice 214 that lies close to the free end 206 of the conduit 204. The spacing of the free end 206 of the conduit 204 from the orifice 214 is preferably between about 0.025 mm and 0.127 mm, preferably being about 0.05 mm, which has been found to produce a Coanda effect when gas is introduced at a rate of between 5 litres per minute and 15 litres per minute.

To produce the Coanda effect the Coanda profile is formed by several inwardly-stepped portions 208 of the free end 206 of the conduit 204 with an angular relationship of between about 25° and 35° from the axis of the conduit as shown most clearly in FIG. 3. When pressurised gas is introduced through the gas port 4 at the preferred flow rate the gas will flow into the space between the conduit 204 and the frusto-conical portion 203 and between the vanes 212 towards the gap between the free end 206 of the conduit 204 and the orifice 214. The gas flows across the Coanda profile 208 creating a high velocity, turbulent flow that effectively entrains ambient air drawn into the air inlet 3 by the inspiratory effort of the patient and directs the flow towards the patient end of the air flow tube 106, as illustrated in FIG. 5. During inhalation, positive air pressure (PAP) is provided to the patient and the flow of ambient air towards the patient is amplified by the Coanda effect.

During exhalation, the expiratory flow generated by the patient overcomes the force of the compressed gas flowing across the Coanda profile so that the Coanda effect ceases. If the one-way valve were positioned between the entrainment device 200 and the O-PEP device 100 the valve would close during exhalation and thereby isolate the entrainment device.

Figure 6A:
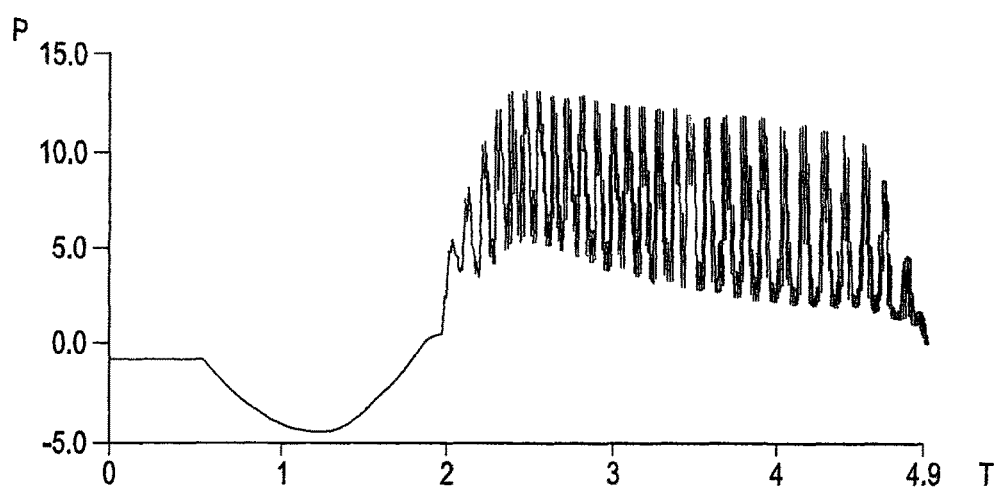
FIGS. 6A to 6C are graphs showing pressure curves.
Figure 6B:
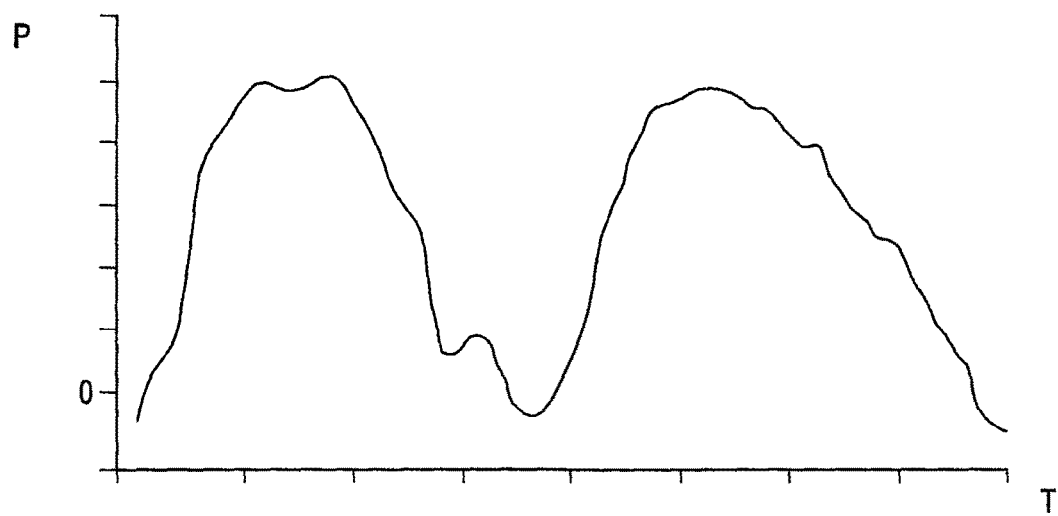
Figure 6C:
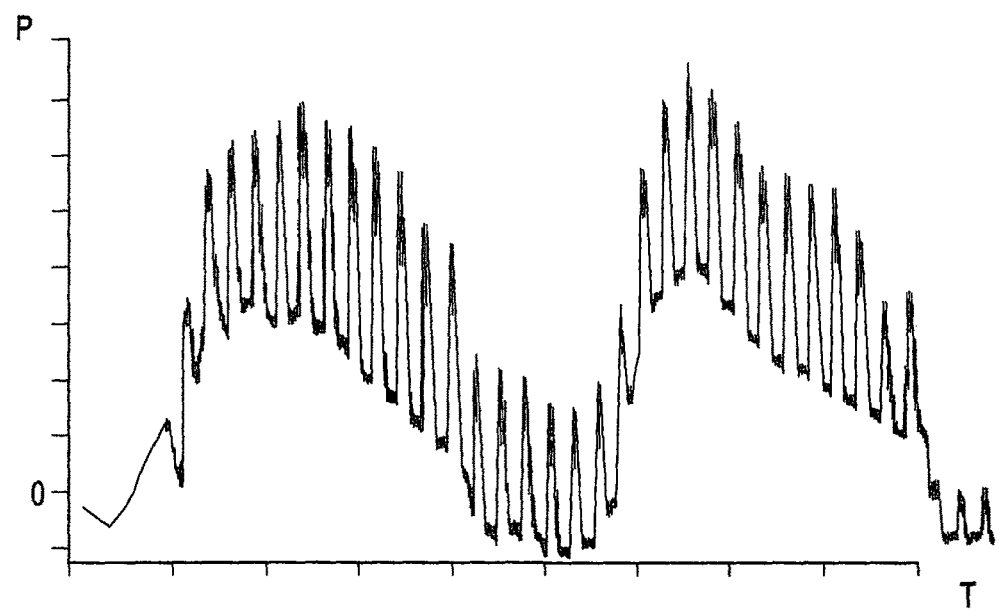

FIG. 6A illustrates a typical pressure/time curve of a conventional O-PEP vibratory device alone showing that the mean inspiratory pressure is negative and that the vibratory effect only occurs during expiration. FIG. 6B illustrates how the air entrainment device 200 would function by itself to provide a mean inspiratory pressure that was positive but without any vibrating or oscillatory therapy effect. FIG. 6C shows the combined effect of the vibratory device 100 with the air entrainment device 200 operational. This combination results in a mean inspiratory pressure that is positive and a vibratory effect that is produced both during patient expiratory and inspiratory phases. This could help patients with some sort of atelectasis or secretion clearance problems.

This positive airway pressure (PAP) is generated by the air entrainment device 200 when gas pressure is supplied to the inlet port 4. Typically, the gas would be air or a gas mixture containing oxygen at higher than atmospheric levels of concentration, such as pure oxygen, and would be supplied at a pressure of around 50 psi ($3.4 \times 10^5$ pascal). The gas could be supplied by a cylinder of compressed gas 119 (FIG. 2), a hospital air or oxygen supply or from a domestic nebuliser compressor although the latter may have lower pressures and reduce the effectiveness of the PAP delivered. Where an oxygen-rich gas is used this mixes with the entrained ambient air to produce an oxygen enriched mixture supplied to the patient.

If gas supply to the air inlet 4 is terminated the positive airway pressure ceases and the apparatus functions as a conventional oscillatory respiratory therapy device. The series arrangement of the air entrainment device 200 and the oscillatory therapy device 100 and the open passage through the air entrainment device enable gas to flow through freely when the air entrainment device is not in operation. Alternatively, it would be possible to lock the oscillatory mechanism 100 closed so that the apparatus functions solely as a positive airway pressure device.

The pressure monitoring port 5 would normally be capped except when pressure monitoring was needed. Alternatively, the port 5 could be connected to a pressure monitor indicator mounted on the apparatus to give the patient or clinician constant information about the pressure levels.

Apparatus according to the present invention can be used by patients who normally have difficulty using conventional oscillatory expiratory therapy devices such as those patients with relatively low expiratory flow capacity.

The invention claimed is:

1. Respiratory therapy apparatus including a respiratory therapy device having a patient interface and a valve arranged to produce an oscillating resistance to expiratory flow through the device, characterised in that the therapy apparatus additionally includes an arrangement for generating a continuous flow of inspiratory respiratory gas to the patient interface, that the arrangement includes a gas inlet arranged to receive a supply of respiratory gas at elevated pressure and an air entrainment device arranged to receive the gas from the inlet to entrain air drawn into the arrangement so as to amplify the flow of air at a positive airway pressure to the patient interface, the apparatus further including a second valve positioned between the respiratory therapy device and the arrangement such that the second valve closes to isolate the air entrainment device during expiratory flow.

2. Apparatus according to claim 1, characterised in that the valve includes a valve element on a rocker arm that opens and closes an opening during exhalation through the apparatus.

3. Apparatus according to claim 1, characterised in that the air entrainment device includes a ring orifice arranged to receive the gas at elevated pressure and to amplify inspiratory gas flow to the patient interface by entraining air through the orifice.

4. Apparatus according to claim 3, characterised in that the ring orifice lies close to a free end of a conduit shaped with a Coanda profile such that a Coanda effect is provided with the gas received at a preferred flow rate to entrain the air drawn into the entrainment device towards the patient interface.

5. Apparatus according to claim 1, characterised in that the respiratory gas at elevated pressure has an oxygen concentration at higher than atmospheric concentrations.

6. Apparatus according to claim 1, characterised in that the apparatus includes an air flow tube opening at one end into the patient interface and opening at its opposite end into the entrainment device, and that the air flow tube opens into the valve arranged to produce an oscillating resistance to expiratory flow through the device at a location between the patient interface and the arrangement for generating a continuous flow of inspiratory respiratory gas.

* * * * *